(12) United States Patent
Ryotokuji

(10) Patent No.: US 9,937,071 B2
(45) Date of Patent: *Apr. 10, 2018

(54) METHOD FOR EXPRESSING GENES ACTIVATING HOMEOSTASIS

(71) Applicant: Kenji Ryotokuji, Chiba (JP)

(72) Inventor: Kenji Ryotokuji, Chiba (JP)

(*) Notice: Subject to any disclaimer, the term of this patent is extended or adjusted under 35 U.S.C. 154(b) by 1043 days.

This patent is subject to a terminal disclaimer.

(21) Appl. No.: 14/026,520

(22) Filed: Sep. 13, 2013

(65) Prior Publication Data

US 2014/0194960 A1 Jul. 10, 2014

Related U.S. Application Data

(60) Provisional application No. 61/701,228, filed on Sep. 14, 2012.

(51) Int. Cl.
*A61F 7/00* (2006.01)

(52) U.S. Cl.
CPC ...... *A61F 7/007* (2013.01); *A61F 2007/0047* (2013.01); *A61F 2007/0086* (2013.01); *A61F 2007/0093* (2013.01)

(58) Field of Classification Search
CPC combination set(s) only.
See application file for complete search history.

(56) References Cited

U.S. PATENT DOCUMENTS

| 5,950,635 A | 9/1999 | Garcia-Rill et al. |
| 2007/0038275 A1* | 2/2007 | Kim ............ A61N 1/326 607/90 |
| 2008/0249587 A1* | 10/2008 | Cho ............ A61H 39/002 607/46 |

\* cited by examiner

*Primary Examiner* — Joseph Stoklosa
*Assistant Examiner* — Adam Avigan
(74) *Attorney, Agent, or Firm* — Westerman, Hattori, Daniels & Adrian, LLP

(57) ABSTRACT

A method for expressing a homeostatic function activating gene, comprising a step of applying a thermal stimulus, which is lower than 50 degrees Celsius, to at least a stimulus application origin part, which is a part between first and second toes of left or right foot sole, and which is located at an intersection of an extended line of a medial edge and a vertical line of the medial malleolus, by using an electric type warm temperature heating stimulus apparatus, thereby increasing a blood volume.

2 Claims, 4 Drawing Sheets

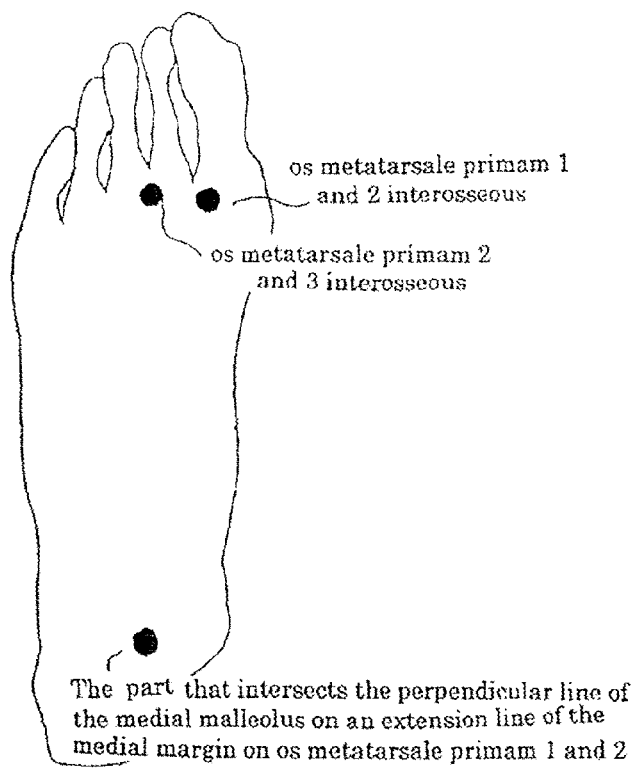

METHOD FOR EXPRESSING GENES ACTIVATING HOMEOSTASIS

CROSS-REFERENCES TO RELATED APPLICATION

This application claims the benefit of U.S. Provisional Application No. 61/701,228, filed Sep. 14, 2012.

BACKGROUND

Technical Field

The present invention relates to a method for expressing a gene, which activates a homeostatic function, by applying a thermal stimulus to a specific local part of a body surface by using an electric type warm temperature heating stimulus apparatus.

Related Art

U.S. Pat. No. 5,950,635 discloses a point surface stimulus method according to a specific acupuncture treatment for reducing anxiousness, for example, stress. The patent discloses that LR3, HT3, and PC6 are specified as stimulus points of patients. Electrodes are brought into contact with these three stimulus points, respectively, thereby passing current through the electrode. Here, the LR3 is located That is, the patent discloses that when the above-mentioned stimulus points (LR3, HT3, and PC6) are stimulated with needles, the P1 potential decreases and anxiousness is reduced. In addition, other than the stimulus points LR3, HT3, and PC6, no stimulus points to be stimulated with the needles are disclosed.

SUMMARY

Technical Problem

Although the US patent discloses a method of stimulating LR3, HT3, and PC6 as stimulus points, no analysis on a human gene by such a stimulus has not made. In view of such circumstances, it is an object of the present invention to offer a method for expressing a gene, which activates a homeostatic function, by applying a thermal stimulus to a thermal-stimulus origin part which is a specific local part of a body surface, using an electric type warm temperature heating stimulus, so that the volume of a blood flow to a peripheral blood pipe or a cerebral blood vessel may be increased by 60% or more, preferably twice to four times that before the stimulus is applied, thereby normalizing splicing or splicing at the time of transfer and carrying out the transfer smoothly.

Solution of Problem

The invention provides a method for expressing a homeostatic function activating gene, comprising the following steps of: applying a thermal stimulus, which is lower than 50 degrees Celsius, to at least a stimulus application origin part, which is part that intersects the perpendicular line of the medial malleolus on an extension line of the medial margin on os metatarsale primam 1 and 2 in foot sole of right and left by using an electric type warm temperature heating stimulus apparatus, thereby increasing a blood volume by 60% or more and preferably twice to force times.

The invention provides a method for expressing a gene, comprising the following steps of: applying a thermal stimulus, which is lower than 50 degrees Celsius, to a live body by using an electric type warm temperature heating stimulus apparatus so that a blood volume is increased by 60% or more of and preferably twice to force times that before the thermal stimulus is applied, whereby by a specific signaling and transcriptional activation factor for determining proliferation and differentiation of a signaling and transcription transport system in which direct transmission to a core is performed by a signal of an extracellular gene of cytokine, intracellular normal protein molecules are maintained so that breakdown of amino acid is controlled, and a gene for activating a homeostatic function, which is a normal immunity action of the living body, is expressed.

The invention provides a method for expressing gene in connection with control of proliferation and differentiation of cells, comprising the following steps of: applying a thermal stimulus, which is lower than 50 degrees Celsius, to a stimulus part of a live body, by using an electric type warm temperature heating stimulus apparatus, thereby increasing a blood volume by 60% or more of and preferably twice to force times that before the thermal stimulus is applied, whereby TNF-alpha acts on cells lining the blood vessels or vascular smooth muscle cells, and causes induction of blood vessel permeability rise and a vasodilatation, through prostaglandin (PG) and NO (nitric oxide).

The invention provides a method for expressing a homeostatic function activating gene, comprising the following steps of: applying a thermal stimulus, which is lower than 50 degrees Celsius, to a stimulus part of a live body, by using an electric type warm temperature heating stimulus apparatus, thereby increasing a blood volume by 60% or more of and preferably twice to force times that before the thermal stimulus is applied, whereby genes for activating a homeostatic function are expressed, and genes for activating a homeostatic function are expressed by switching the genes on expression.

The invention provides a method for expressing gene, comprising the following steps of applying a thermal stimulus, which is lower than 50 degrees Celsius, to a stimulus part of a live body, by using an electric type warm temperature heating stimulus apparatus, so as to increase a blood volume by 60% or more of and preferably twice to force times that before the thermal stimulus is applied, thereby expressing, as to circulatory organ disease, a genes which causes an increase of functional cells is expressed, a promotion of cellular proliferation or functional differentiation, an activation of a hematopoietic system and an immunity system, an activation of cells with respect to cancer immunity or inflammation, metabolism and proliferation of functional cells, an improvement in responsiveness to hormone, and proliferation of vascular endothelium and a cardiac muscle, or functional control.

The invention provides a method for expressing gene, comprising the following steps of applying a thermal stimulus, which is lower than 50 degrees Celsius, to a stimulus part of a live body, by using an electric type warm temperature heating stimulus apparatus, thereby expressing, as to cancer disease, a genes which causes an increase of functional cells, a promotion of cellular proliferation or functional differentiation, an activation of a hematopoietic system and an immunity system, an activation of cells with respect to cancer immunity or inflammation, metabolism and proliferation of functional cells, an improvement in responsiveness to hormone, and a promotion of osteogenic activity, proliferation of vascular endothelium and a cardiac muscle, or change in functional control.

The invention provides a gene expressed by the method for expressing a gene. The invention provides a blood volume increasing system for carrying out the method for expressing a gene.

The invention provides a blood volume increasing system, wherein a thermal stimulus, which is lower than 50 degrees Celsius, is applied to a part which intersects the perpendicular line of the medial malleolus on an extension line of the medial margin on os metatarsale primam 1 and 2 in foot sole of right and left.

Advantageous Effects of the Invention

According to the method of the invention for expressing a gene, a thermal stimulus to a live body by using an electric type warm temperature heating stimulus apparatus is applied, so that a blood volume in a peripheral blood vessel or a cerebral blood vessel is increased by 60% or more of and preferably twice to force times that before the thermal stimulus is applied, In the present invention, the increase of the volume of blood flow to the peripheral blood vessels and the cerebral blood vessels, improves stress due to a decrease of cortisol and ACTH, which are stress hormones; increases deep body temperature; decreases the blood sugar level; decreases total cholesterol and HDL cholesterol; improves depression, dementia, sudden deafness, cataract, or knee osteoarthritis, and improves a memorizing faculty.

BRIEF DESCRIPTION OF THE DRAWINGS

FIG. 5 is a schematic diagram showing thermal-stimulus origin parts of left and right soles; and FIG. 6 is a schematic diagram showing one cycle of a thermal-stimulus pattern.

DESCRIPTION

Figure 1:
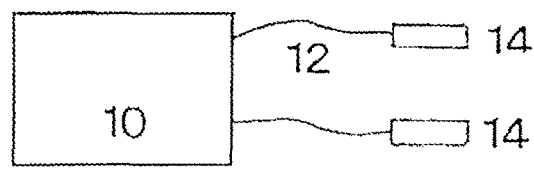
FIG. 1 is a schematic diagram showing an electric type warm temperature heating stimulus apparatus used for the present invention.

According to the method of the invention for expressing a gene, by using an electric type warm temperature heating stimulus apparatus so that a blood volume in a peripheral blood vessel or a cerebral blood vessel is increased by 60% or more of and preferably twice to force times that before the thermal stimulus is applied, whereby by a specific signaling and transcriptional activation factor for determining proliferation and differentiation of a signaling and transcription transport system in which direct transmission to a core is performed by a signal of an extracellular gene of cytokine, intracellular normal protein molecules are maintained so that breakdown of amino acid is controlled, and a gene for activating a homeostatic function, which is a normal immunity action of the living body, is expressed.

According to the method of the invention, by increasing a blood volume, TNF-alpha acts on cells lining the blood vessels or vascular smooth muscle cells, and causes induction of blood vessel permeability rise and a vasodilatation, through prostaglandin (PG) and NO (nitric oxide).

A gene for activating a homeostatic function expressed by increasing blood volume is switched on.

When the gene is switched on, the gene act as following.

To activate genes which control cellular proliferation and differentiation through cytokine, such as interleukin (IL-6).

To express interleukin (IL-6), G-protein-coupled receptor (GPCRs), B Cell, TNF-alpha, and p38MAPK.

To express vasoactive intestinal peptide (VIP) induced by STAT or MAPK.

To improve control insufficiency of a JAK/STAT pathway, to induce an activation thereof, and then to induct an activation of a target gene.

To have VEGF raise a secretion or to get involved in expression of VIP.

To improve a suppression of a function of STAT protein in a JAK/STAT signal transport system.

To make a suppression of a function of STAT protein.

To have intracellular STAT protein bind to a receptor and to improve a transfer of information from cytokine of a cell membrane to a gene in a nucleus.

To suppress a point mutation of genes in a wild type gene sequence and an expression of abnormal genes due to deletion or insertion. In a state where JAK and STAT bind to each other, genes are expressed in response to a stimulus to cytokine, such as interferon, and controls normal splicing at time of transfer. Which one of positive feedback mechanism and negative feedback mechanism is strongly inducted by the stimulus of cytokine, depends on the intensity of the stimulus, and when it receives a lot of stimulus by the cytokine, a negative feedback mechanism which suppresses an excessive signal, operates.

A cell has a system which controls a signal of the cytokine so as to be positive or negative, and plays an important role for maintenance of homeostasis.

Induction of STAT1 or ISG15 due to interferon as a positive feedback mechanism, is recognized. On the other hand, there are repression pathways of a cytokine signal, such as reduction of the receptor expression due to protein decomposition, dephosphorylation of JAK and STAT due to SHP, and functional inhibition of STAT due to the protein.

According to the present invention, when the volume of blood flow increases, functional cells are increased by an expression of genes which get engaged in a signal receptor between cells; the cellular proliferation and functional differentiation are promoted by an expression of the genes which get engaged in cell proliferation/differentiation control; hematogenesis and hematopoietic differentiation is activated by an expression of genes which get engaged in hematogenesis and hematopoietic differentiation; cells which get engaged in an activation of inflammation and immunity systems are activated; functional cells are metabolized and increased by an expression of genes which get engaged in cell proliferation and metabolism; the responsiveness to hormone is improved by an expression of genes which get engaged in endocrine system control; an osteogenetic activity is promoted by an expression of genes which get engaged in an osteogenetic system control; and a vascular endothelium and cardiac muscle by an expression of genes which get engaged in cellular proliferation and metabolism of a circulatory organ system is increased, and further a functional control changes.

It has been confirmed that interleukin, a G-protein-coupled receptor (GPCR), B Cell, TNF-alpha, and p38MAPK are expressed with high frequency as 0.005 or more significant genes in gene pathway analysis.

Tables 1-1 to 1-4 show WiKiPathways data of patients having symptom of acute diarrhea, a liver cancer, physical feebleness, cardiac dysfunction, or an extreme stress.

1. Disease Name; Physical feebleness

Stimulated parts; os metatarsale primam 3 and 4 interosseous of soles Method of stimulus; Warm heating Method of Stimulus; Warm Heating Improved test results; Decrease of insulin and decrease of vascular endothelial growth factor

TABLE 1-1

| Pathway Name | Changed Genes | Total Genes | Z score | P-value |
|---|---|---|---|---|
| Hs_Cytoplasmic_Riboasomal_Proteins_WP477_41118 | 9 | 73 | 4376 | 0.000907361 |
| Hs_Translation_Factors_WP107_41026 | 6 | 42 | 4035 | 0.003493526 |
| Hs_p38_MAPK_Signaling_Pathway_WP400_45281 | 4 | 33 | 2875 | 0.027441757 |
| Hs_IL-6_signaling_pathway_WP364_44627 | 4 | 39 | 2469 | 0.044486637 |
| Hs_MicroRNAs_in_cardiomyocyte_hypertrophy_WP1544_44907 | 6 | 80 | 2145 | 0.051602509 |
| Hs_TGF_beta_Signaling_Pathway_WP366_44604 | 8 | 112 | 2324 | 0.053241108 |
| Hs_TNF_alpha_Signaling_Pathway_WP231_44640 | 6 | 83 | 2045 | 0.059206884 |

2. Disease Name; Cardiac dysfunction
Stimulated pans; os metatarsale primam 1 and 2 interosseous
Method of Stimulus; Warm Heating
Improved test results; Decrease of insulin and decrease of vascular endothelial growth factor

TABLE 1-2

| Pathway Name | Changed Genes | Total Genes | Z score | P-value |
|---|---|---|---|---|
| Hs_Calcium_Regulation_in_the_Cardiac_Cell_WP536_41204 | 9 | 145 | 3026 | 0.008380279 |
| Hs_GPCRs,_Class_C_Metabotropic_glutamato,_phoromono_WP501_41097 | 2 | 14 | 2925 | 0.051714709 |

3. Disease Name; Liver cancer
Stimulated parts; intersects the perpendicular line of the medial malleolus on an extension line of the medial margin on os metatarsale primam 1 and 2 in foot sole
Method of Stimulus; Heating
Improved test results; Decrease of TTT, decrease of ZTT and decrease of amylase

TABLE 1-3

| Pathway Name | Changed Genes | Total Genes | Z score | P-value |
|---|---|---|---|---|
| Hs_Hedgehog_Signaling_Pathway_WP47_44618 | 2 | 16 | 3825 | 0.023866483 |
| Hs_Glutathione_metabolism_WP100_41200 | 2 | 17 | 3682 | 0.026448264 |
| Hs_GI_to_S_cell_control_WP45_41128 | 3 | 65 | 2247 | 0.062977426 |

4. Disease Name; Extreme stress
Stimulated parts; intersects the perpendicular line of the medial malleolus on an extension line of the medial margin on os metatarsale primam 1 and 2 in foot sole
Method of Stimulus; Heating
Improved test results; Decrease of neutral fat, decrease of TTT, decrease of insulin, and increase of ACTH

TABLE 1-4

| Pathway Name | Changed Genes | Total Genes | Z score | P-value |
|---|---|---|---|---|
| Hs_GPcRs,_0ther_WP117_45105 | 5 | 82 | 2246 | 0.047308933 |

Table 2 shows a list of pathways of gene analysis of healthy adults.

TABLE 2

>Healthy Adult Gene Analysis *p-value significance 0.005 or more
[A table of common healthy adult pathways]

| No | Pathway | Note |
|---|---|---|
| 1 | Hs_GPcRs,_0ther_WP117_45105 | Marker in connection with control of proliferation or differentiation of cells |
|  | Hs_GPCRs,_Class_C_Metabotropic_glutamato,_phoromono_WP501_41097 |  |
| 2 | Hs_Elcotron_Transport_Chain_WP111_63179 | Marker which suggests an activation of proliferation and metabolism of cells |
| 3 | Hs_Cytoplasmic_Riboasomal_Proteins_WP477_41118 |  |
| 4 | Hs_Cholesterol_Biosynthesis_WP197_4122 |  |
| 5 | Hs_Translation_Factors_WP107_41026 |  |
| 6 | Hs_p38_MAPK_Signaling_Pathway_WP400_45281 |  |
| 7 | Hs_B_Cell_Receptor_Signaling_Pathway_WP23_63145 | Marker which suggests an activation of an immunity system |
| 8 | Hs_TNT_alpha_Signaling_Pathway_WP231_44640 |  |
| 9 | Hs_TGF_beta_Signaling_Pathway_WP366_44604 |  |

TABLE 2-continued

>Healthy Adult Gene Analysis *p-value significance 0.005 or more
[A table of common healthy adult pathways]

| No | Pathway | Note |
|----|---------|------|
| 10 | Hs_Calcium_Regulation_in_the_Cardiac_Cell_WP536_41204 | |
| 11 | Hs_amino_acid_conjugation_of_benzoic_acid_WP521_41176 | |
| 12 | Hs_MicroRNAs_in_cardiomyocyte_hypertrophy_WP1544_44907 | |
| 13 | Hs_IL-6_signaling_pathway_WP364_44627 | |

By the gene analysis, a marker (1) in connection with control of proliferation or differentiation, markers (2-6) that suggest an activation of cellular proliferation or metabolism, and markers (7-9) which suggest an activation of an immunity system, were recognized Table 3 shows a list of pathways of gene analysis of cancer patients.

TABLE 3

Gene Analysis of Cancer Patients
[A table of common cancer pathways]

| | Pathway |
|---|---------|
| | Hs_IL-3_Signaling_Pathway_WP286_44623 |
| | Hs_IL-3_Signaling_Pathway_WP286_44623 |
| | Hs_IL-6_signaling_pathway_WTP364_44627 |
| | Hs_IL-6_signaling_pathway_WP364_44627 |
| 2 | Hs_Adipogenesis_WP236_41040 |
| | Hs_Adipogenesis_WP236_41040 |
| 3 | Hs_Arrhythmogenic_right_ventricular_cardiomyopathy_WP2118_47057 |
| | Hs_Arrhythmogenic_right_ventricular_cardiomyopathy_WP2118_47057 |
| 4 | Hs_Diurnally_regulated_genes_with_circadian_orthologs_WP410_41104 |
| | Hs_Diurnally_regulated_genes_with_circadian_orthologs_WP410_41104 |
| 5 | Hs_EGF-EGFR_Signaling_Pathway_WP437_44600 |
| | Hs_EGF-EGFR_Signaling_Pathway_WP437_44600 |
| 6 | Hs_Endochondral_Ossification_WP474_45000 |
| | Hs_Endochondral_Ossification_WP474_45000 |
| 7 | Hs_GPCRs_Class_A_Rhodopsin-like_WP455_41121 |
| | Hs_GPCRs,_Class_C_Metabotropic_glutamate,_pheromone_WP501_41097 |
| 8 | Hs_Kit_receptor_signaling_pathway_WP304_44603 |
| | Hs_Kit_receptor_signaling_Pathway_WP304_44603 |
| 9 | Hs_p38_MAPK_Signaling_Pathway_WP400_45281 |
| | Hsp_38_MAPK_Signaling_Pathway_WP400_45281 |
| 10 | Hs_Signaling_of_Hepatocyte_Growth_Factor_Receptor_WP313_41206 |
| | Hs_Signaling_of_Hepatocyte_Growth_Factor_Receptor_WP313_41206 |
| 11 | Hs_Synthesis_and_Degradation_of_Ketone_Bodies_WP311_43510 |
| 12 | Hs_TNF_alpha_Signaling_Pathway_WP231_44640 |
| 13 | Hs_Tryptophan_metabolism_WP465_43616 |
| 14 | Hs_Regulation_of_Actin_Cytoskeleton_P51_45278 |
| 15 | Hs_miRs_in_Muscle_Cell_Differentiation_WP2012_44910 |
| 16 | Hs_Osteoblast_Signaling_WP322_45323 |
| 17 | Hs_Calcium_Regulation_in_the_Cardiac_Cell_WP536_41204 |
| 18 | Hs_Focal_Adhesion_WP306_41071 |
| 19 | Hs_Glutathione_metabolism_WP100_41200 |
| 20 | Hs_Hedgehog_Signaling_Pathway_WP47_44618 |

Markers (1, 2, 4, 5, 6, 8, 9, and 10) which suggest biliary tract cancer were recognized. Especially the markers (5, 8, 9, and 10) in connection with differentiation or proliferation of a hematopoietic stem cell of bone marrow and the inflammation markers (1, and 12) suggest an activation of an immunity system. A possibility was estimated so that with an increase in a blood flow, blood cells and blood were supplied to the inside of the cancer tissue through blood vessels led in the cancer tissue so that a supply of a lymphocyte increased whereby antitumor immunity was activated.

Table 4 shows a list of pathways of gene analysis of patients of a cardiovascular disease.

TABLE 4

Gene analysis of cardiovascular disease patients
[A list of common pathways of cardiovascular disease]

| No. | Pathway |
|-----|---------|
| | Hs_IL-2_Signaling_pathway_WP49_44622 |
| | Hs_IL-3_Signaling_Pathway_WP286_63210 |

TABLE 4-continued

Gene analysis of cardiovascular disease patients
[A list of common pathways of cardiovascular disease]

| No. | Pathway |
|-----|---------|
| | Hs_IL-7_signaling_pathway_WP205_45139 |
| | Hs_Wnt_Signaling_Pathway_WP363_45009 |
| | Hs_Wnt_Signaling_Pathway_WP428_43042 |
| 3 | Hs_B_Cell_Receptor_Signaling_Pathway_WP23_44620 |
| 4 | Hs_Cell_cycle_WP179_45137 |
| 5 | Hs_DNA_damage_response_(only_ATM_dependent)_WP710_33421 |
| 6 | Hs_EGF-EGFR_Signaling_Pathway_WP437_44600 |

TABLE 4-continued

Gene analysis of cardiovascular disease patients
[A list of common pathways of cardiovascular disease]

| No. | Pathway |
|---|---|
| 7 | Hs_ErbB_signaling_pathway_WP673_29836 |
| 8 | Hs_Glutathione_metabolism_WP100_41200 |
| 9 | Hs_GPCRs,_Class_A_Rhodopsin-like_WP455_63203 |
| 10 | Hs_Hedgehog_Signaling_Pathway_WP47_44618 |
| 11 | Hs_Integrated_Breast_Cancer_Pathway_WP1984_44857 |
| 12 | Hs_Leptin_signaling_pathway_WP2034_44631 |
| 13 | Hs_MAPK_signaling_pathway_WP382_41048 |
| 14 | Hs_MicroRNAs_in_cardiomyocyte_hypertrophy_WP1544_44907 |
| 15 | Hs_mRNA_processing_WP411_45374 |
| 16 | Hs_Osteopontin_Signaling_WP1434_45316 |
| 17 | Hs_Oxidative_phosphorylation_WP623_59095 |
| 18 | Hs_Prolactin_Signaling_Pathway_WP2037_46067 |
| 19 | Hs_Signaling_of_Hepatocyte_Growth_Factor_Receptor_WP313_45129 |
| 20 | Hs_Striated_Muscle_Contraction_WP383_41139 |
| 21 | Hs_TCR_Signaling_Pathway_WP69_45093 |
| 22 | Hs_Translation_Factors_WP107_45069 |
| 23 | Hs_Triacylglyceride_Synthesis_WP325_43910 |
| 24 | Hs_Tryptophan_metabolism_WP465_43616 |
| 25 | Hs_TSH_signaling_pathway_WP2032_44635 |

A significant rise was observed in the cell proliferation system markers (4, 5, 6, 8, 9, 11, 13, 15, 17, 19, 22, 23, and 24) and the cell functional differentiation system markers (2, 3, 6, 7, 14, 17, 18, 19, and 21). Especially, the markers (1, 2, 3, 6, 7, and 21) in connection with proliferation or differentiation of cells from the immune system suggest an activation of an immune system, and the markers (12, and 18) relating to a hormone receptor suggest a reinforcement of entire body control according an endocrine system. It is thought that an increase in a blood flow is brought about by inducing a blood vessel permeability rise and vasodilatation through nitric oxide.

Table 5 shows the measurement data of the blood flow volume of each patient of condition of physical feebleness, cardiac dysfunction, and an extreme stress.

TABLE 5

| Patient | Blood flow volume before stimulus application | Blood flow volume after stimulus application | Rate of increase % |
|---|---|---|---|
| No. 1 | 1.287 | 2.1036 | 63 |
| No. 2 | 3.2791 | 8.0098 | 144 |
| No. 3 | 1.7603 | 2.959 | 68 |
| No. 4 | 2.8101 | 4.6872 | 68 |
| No. 5 | 5.9857 | 13.0065 | 117 |
| No. 6 | 3.453 | 6.9631 | 102 |
| No. 7 | 2.0954 | 4.7401 | 126 |
| No. 8 | 1.4332 | 3.5227 | 146 |
| No. 9 | 1.0091 | 1.7377 | 72 |
| No. 10 | 3.9592 | 8.0699 | 104 |
| No. 11 | 1.5635 | 3.8743 | 148 |

A blood flow increase system for applying a thermal stimulus using an electric type warm temperature heating stimulus apparatus according to the present invention, is an epoch-making product obtained from day-to-day research done by the present inventor, in which a thermal-stimulus origin part, which is a local part of a body surface which plays a role for increasing blood flow volume to a peripheral blood vessel or a cerebral blood vessel, is identified, and two or more thermal-stimulus origin parts are combined so as to apply thermal stimulus. According to the present invention, such a blood flow increase system identifies thermal-stimulus origin parts, which have not been known until now, where blood flow volume is increased, and applies thermal stimuli, to the combined two or more thermal-stimulus origin parts.

Preferably, by using a blood flow volume increasing system, stimuli are simultaneously or non-simultaneously applied to at least two thermal-stimulus origin parts, preferably applied to four pans, which are independent of each other, and are different from each other. Moreover, it is desirable that the stimuli be preferably applied to the at least two parts, preferably four parts, by shifting phases thereof. It is desirable that the stimuli be applied thereto in the same warm temperature heating pattern.

According to the present invention, thermal stimuli are applied to the thermal-stimulus origin parts of a body surface by the electric type warm temperature heating stimulus apparatus, and the volume of blood flow is measured by a laser Doppler tissue rheometer, thereby obtaining the increase rate of blood flow volume before and after the application of thermal-stimulus.

Here, it is desirable to measure the volume of blood flow by the laser Doppler tissue rheometer which is attached to an inner and central part of a wrist joint. In a laser tissue blood flowmeter ALF21D (manufactured by ADOVANS), when a living tissue is irradiated with semiconductor laser light (whose wavelength is 780 nm), light reflected from the tissue is convened into an electric signal and the electric signal is processed, thereby obtaining the blood flow information. A C type laser probe (10 mm in diameter, 3 mm in thickness, 2 mm2 in a laser irradiation area, and 1 mm in measurement depth) of the laser tissue blood flowmeter ALF21D was attached to a central part of a wrist joint horizontal line of a healthy adult, and change of the blood flow volume was measured, taking a 15-minute rest after a stimulus.

As to the principle of the laser tissue blood flow volume measurement, laser light collides with red blood cells, which flow through the inside of blood vessels, and the Doppler shift (frequency change), which is produced when receiving dispersion, is used. This measurement method is characterized by non-invasive and real time responsiveness and a capability of consecutive measurement. Furthermore, the ALF21D, which was used this time, can display a blood flow volume on ml/min/100 g scale. This is because signal processing is performed based on the theory of Bonner et al.

FIG. 5 is a schematic diagram showing the thermal-stimulus origin parts of a body surface comprising part (1-1) of os metatarsale primam 1 and 2 interosseous, part (1-2) os metatarsale primam 2 and 3 interosseous, and part (1-3) that intersects the perpendicular line of the medial malleolus on an extension line of the medial margin on os metatarsale primam 1 and 2 in foot sole of right and left.

The thermal-stimulus origin parts of a body surface comprises at least one of part (1-1) at os metatarsale primam 1 and 2 interosseous, part (1-2) at os metatarsale primam 2 and 3 interosseous, and part (1-3) that intersects the perpendicular line of the medial malleolus on an extension line of the medial margin on os metatarsale primam 1 and 2 in foot sole of right and left and in addition an acupuncture point ②TE4, ③ CV12, ④DST16, and ⑤K16.

The blood volume increasing system is performed by at the same time or intermittently applying to thermal stimulus at the thermal stimulus origin parts of a body surface. The blood volume increasing system is performed by combining the thermal stimulus origin parts of a body surface as following; (A) part (1-3) that intersects the perpendicular line of the medial malleolus on an extension line of the medial margin on os metatarsale primam 1 and 2 in foot sole of right, (B) part (1-3) that intersects the perpendicular line of the medial malleolus on an extension line of the medial margin on os metatarsale primam 1 and 2 in foot sole of right and left and in addition an acupuncture point ②TE4, and ⑤K16. (C) part (1-3) that intersects the perpendicular line of the medial malleolus on an extension line of the medial margin on os metatarsale primam 1 and 2 in foot sole of right and in addition an acupuncture point ③CV12, and ④ST16.

The combination of the thermal stimulus origin parts of a body surface is not limited the above the combination.

By applying a thermal stimulus, which is lower than 50 degrees Celsius, to a live body by using an electric type warm temperature heating stimulus apparatus, a blood volume is increased by 60% or more of and preferably twice to force times that before the thermal stimulus is applied, whereby a gene for activating a homeostatic function, which is a normal immunity action of the living body, is expressed and the gene is switched on.

In order to search thermal-stimulus origin parts, it is desirable to use a part searching apparatus. Terminals of this part searching apparatus are brought into contact with a body surface and current flowing between the terminals is measured. And it is desirable that parts where a needle of an ammeter indicates 20-40 µA or more be identified as thermal-stimulus origin parts.

Embodiment

Figure 2:
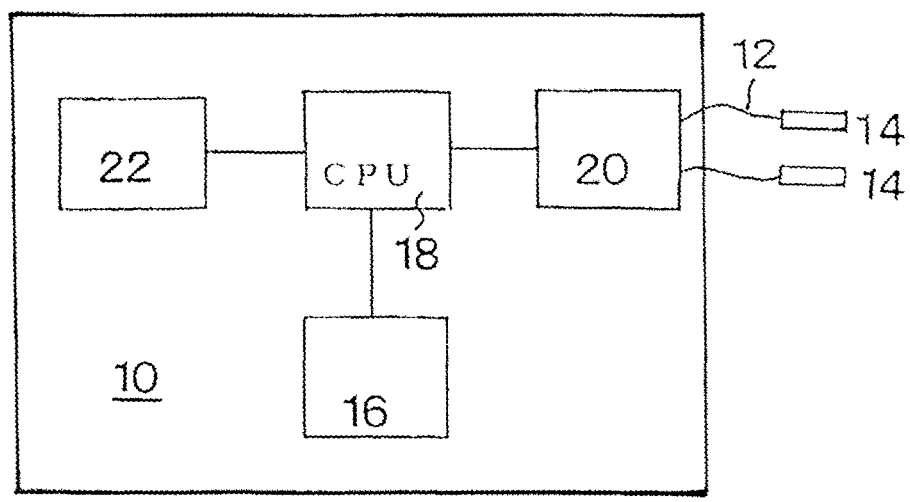
FIG. 2 is a schematic diagram showing a circuit diagram of the electric type warm temperature heating stimulus apparatus of FIG. 1.

FIG. 1 is a schematic view of an electric type warm temperature heating apparatus used for the present invention. FIG. 2 is a schematic view of a circuit diagram of the electric type warm temperature heating apparatus.

A electric type warm temperature heating apparatus comprises the apparatus 10, and a guide element 14 for a thermal stimulus, which is connected to the apparatus 10 by a lead 12.

As shown, the apparatus 10 includes a memory unit 16, in which thermal stimulus patterns are stored, a control unit (CPU) 18, which reads out a thermal stimulus pattern from the memory unit 16, and an output unit 20, which supplies the thermal stimulus pattern to the guide element 14 for a thermal stimulus. A thermal stimulus is applied to a part to be stimulated, according to the thermal stimulus pattern.

A control unit (CPU) 18 is connected to the memory unit 16. A thermal stimulus pattern for obtaining a stimulus condition equivalent to that obtained from combustion of moxa is stored in the memory unit 16. The control unit (CPU) 18 reads out the thermal stimulus pattern from the memory unit 16, controls an output to a heating element(s) based on detection of a temperature sensor 22, and outputs the thermal stimulus pattern to the guide element(s) for a thermal stimulus.

The apparatus 10 is connected to two or more guide elements for a thermal stimulus in order to supply the thermal stimulus pattern to at least two different areas to be stimulated. In this manner, the thermal stimulus pattern is applied to the areas to be stimulated, through the guide elements for thermal stimulus.

A temperature sensor is provided in a predetermined position of the housing which is in contact with a part of a human body, and detects the temperature of the position, so as to send a detection signal to a sensor amplifier. The control unit (CPU) controls an output of an electric power generating circuit so that the temperature of the portion, which is in contact with a skin surface of a human body contact, may not exceed a predetermined temperature. In the warm temperature heating apparatus, the surface temperature of the guide elements for a thermal stimulus is controlled so as to be in a range from 40 to 50±5 degrees Celsius.

When the heating temperature of the heating elements detected by the temperature sensor is equal to or lower than a reference temperature, a positive side period of a pulse signal is controlled so as to be long and a negative side period of the pulse signal is controlled so as to be short, according to the output of the temperature sensor. On the contrary, when it is in a state at the reference temperature, a positive side period is controlled so as to be short and a negative side period thereof is controlled so as to be long.

The electric type warm temperature heating apparatus comprises thermal stimulus control device, the thermal stimulus control device controls at least one of thermal stimulus waveform, heating temperature, thermal stimulus strength, thermal applied time, thermal stimulus cycle, thermal stimulus pattern, heating mode, thermal stimulus protocol. The information from the thermal stimulus control device is output from a guide element 14 for a thermal stimulus.

Figure 3:
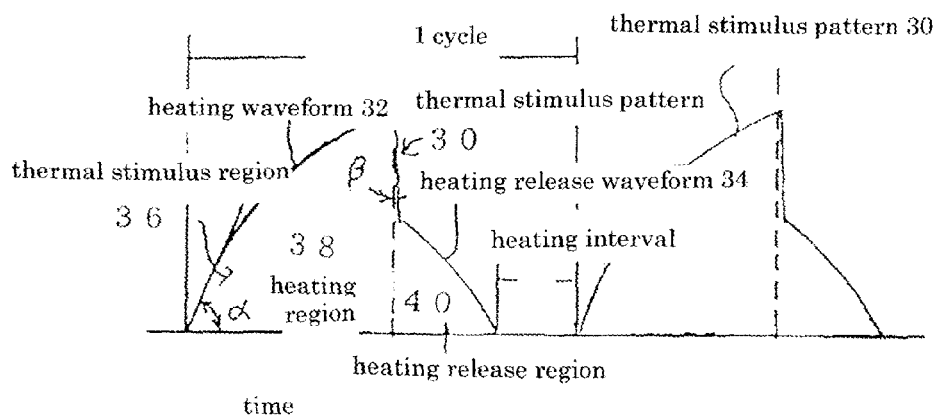
FIG. 3 is a schematic diagram showing a thermal stimulus waveform.

FIG. 3 shows a desirable thermal stimulus waveform, which is obtained by controlling the electric type warm temperature heating apparatus. The thermal stimulus waveform includes a heating waveform 32 obtained by heating it to a predetermined peak temperature, for example, 50±5 degrees Celsius, and a heat release waveform 34 which is formed by stopping heating after it reaches the peak temperature.

A region surrounded by a heating waveform 32 and a heat release waveform 34 is a thermal stimulus region. The thermal stimulus region provides a heating region 38 and a heat release region 40.

The heating waveform 32 may be a convex shape heating waveform obtained by heating it to a predetermined peak temperature, for example, 50±5 degrees Celsius Moreover, the heating waveforms are not limited to the above-described heating waveform. It may be a saw-toothed shape waveform, and concavo-convex waveform. Moreover, the heating waveform and the heat release waveform may be formed as a sine waveform.

The thermal stimulus pattern comprises first thermal stimulus pattern provided region 36 comprising the heating waveform 32, the heat release waveform 34 and a interval between next thermal stimulus region 36 and second thermal stimulus pattern 40 formed by shifting the phase from first thermal stimulus pattern.

A cycle pattern of a thermal stimulus includes a thermal stimulus waveform made up of a warm heating waveform and a heat release waveform, and an interval before the next warm heating curve.

One cycle pattern of the thermal stimulus is desirably set so that a thermal stimulus region may be 10 second to 30 second and an interval between the heating regions may be 1 second to 10 seconds as shown FIG. 6.

The pattern of thermal stimulus desirably includes independent thermal stimulus waveforms whose phases are shifted so that the patterns of thermal stimulus do not substantially overlap each other. That is, as shown in the figures, the pattern of thermal stimulus includes a first thermal stimulus pattern including an interval between a thermal stimulus region and the next thermal stimulus region, and a second thermal stimulus pattern, which includes a thermal stimulus region during a certain period of an interval of the first thermal stimulus pattern and an interval in a first thermal stimulus region.

A temperature sensor is provided in a predetermined position of the housing which is in contact with a part of a human body, and detects the temperature of the position, so as to send a detection signal to a sensor amplifier. The control unit (CPU) controls an output of an electric power generating circuit so that the temperature of the portion, which is in contact with a skin surface of a human body contact, may not exceed a predetermined temperature. In the warm temperature heating apparatus, the surface temperature of the guide elements for a thermal stimulus is controlled so as to be in a range from 40 to 50±5 degrees Celsius.

When the heating temperature of the heating elements detected by the temperature sensor is equal to or lower than a reference temperature, a positive side period of a pulse signal is controlled so as to be long and a negative side period of the pulse signal is controlled so as to be short, according to the output of the temperature sensor. On the contrary, when it is in a state at the reference temperature, a positive side period is controlled so as to be short and a negative side period thereof is controlled so as to be long.

At least a stimulus application origin part use the part (1-3) that intersects the perpendicular line of the medial malleolus on an extension line of the medial margin on os metatarsale primam 1 and 2 in foot sole of right and left and a part ③ and a part ④. A warm temperature heating guide elements of diameter 15 mm is attached on a stimulus application origin part. A heating stimulus is applied to a stimulus application origin part for 15 minutes at 50±5 degrees Celsius.

Figure 4:
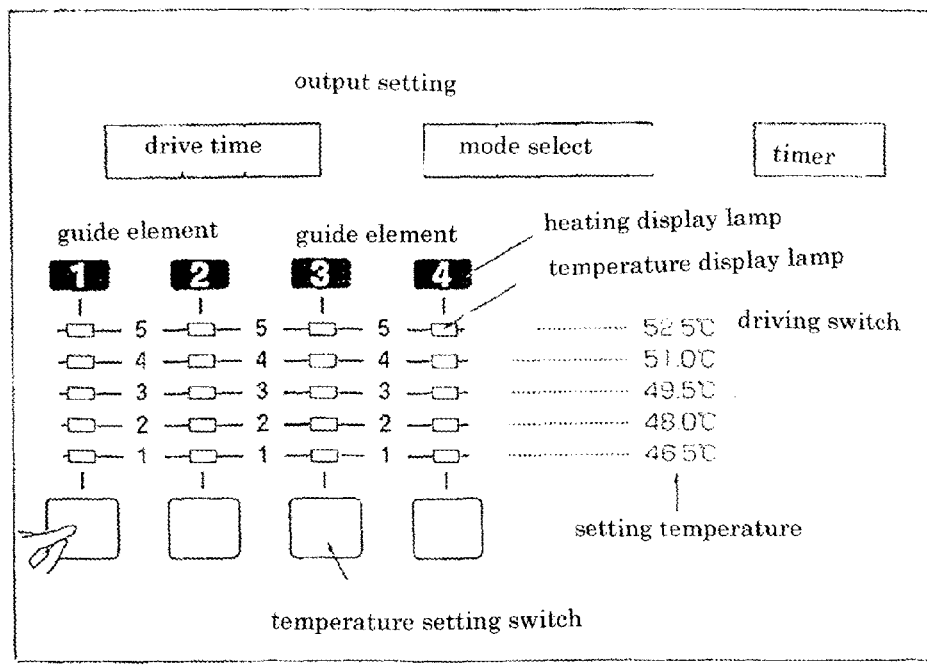
FIG. 4 is a schematic diagram showing a control panel for a warm temperature heating stimulus of an electric type warm temperature heating stimulus apparatus.
Figure 7:
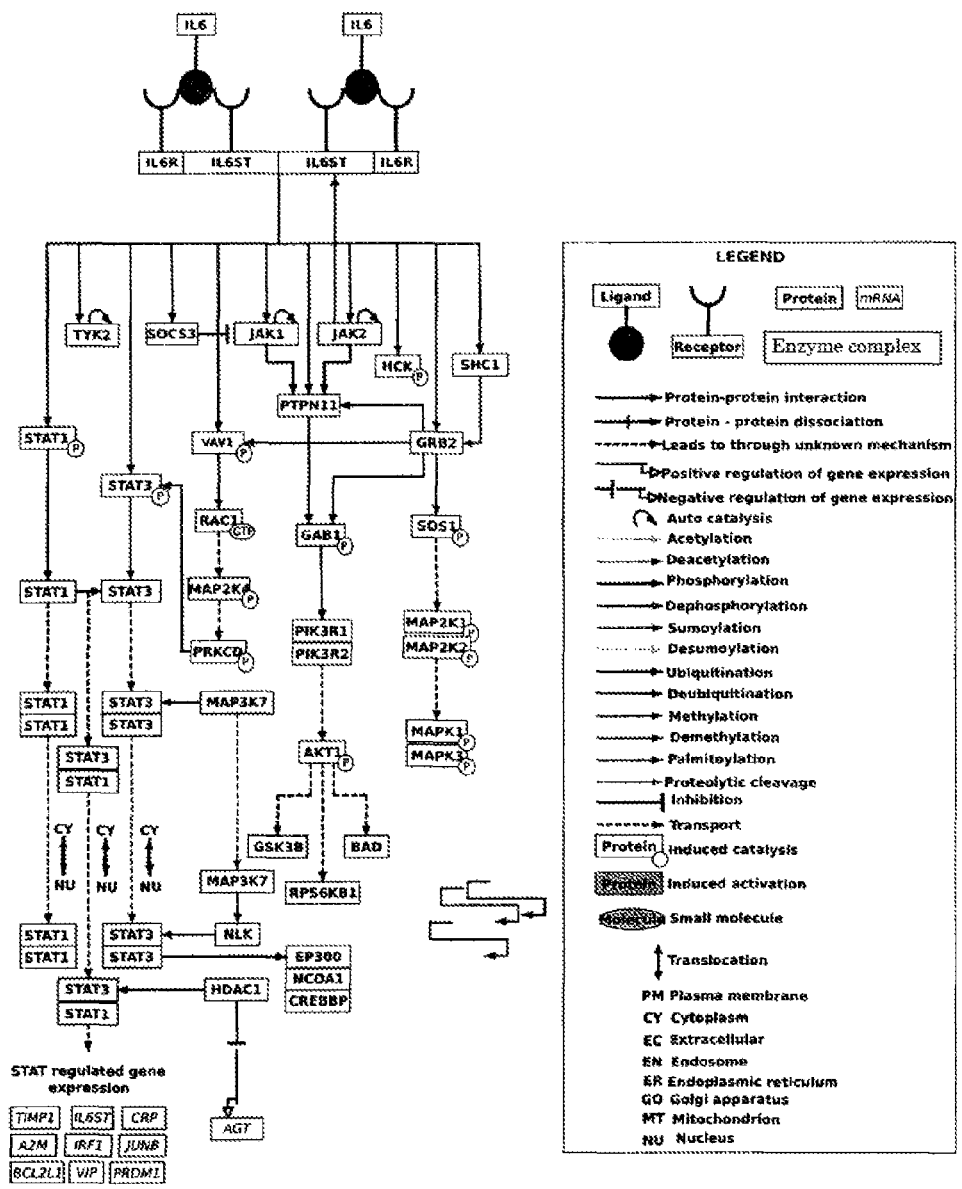
FIG. 7 shows data of signaling pathway of IL-6.

FIG. 4 is a schematic diagram of a control panel for a warm temperature heating stimulus performed by an electric type warm temperature heating stimulus apparatus. Description of the case where warm temperature heating guide elements are fixed to four thermal-stimulus origin parts, which are different from one another, will be given below. The four warm temperature heating guide elements are fixed to the above-mentioned selected parts, and electric power is supplied to the warm temperature heating stimulus apparatus. Here, in temperature setting and stimulus application method of the warm temperature heating guide elements, when the number of thermal-stimulus origin parts is four, the warm temperature heating guide elements 1, 2, 3, and 4 are used. The temperature is adjusted by a temperature setting switch. Every time the switch is pushed, the temperature of the elements is controlled in a range of from 46.5 to 52.5° C. in order of 1-2-3-4-5.

A mode selection button for selecting a warm heating mode, that is, an alternate mode or a sequential mode, is provided therein. In the alternate mode, heating and pausing of the four warm temperature heating guide elements 1, 2, 3, and 4 are alternatively repeated. In the sequential mode, heating of the four warm temperature heating guide elements which are different from one another is carried out one by one in order. In this way, warm temperature heating is nonsimultaneously applied to the four different parts independently of one another. In addition, a mode of a heating interval (time) can be chosen.

The heat conduction plate of the warm temperature heating guide elements are made of at least two kinds of materials whose thermal conductivities are different from each other. The thermal conductivities of the materials at approximately room temperature will be described below. In the present invention where the at least two kind of materials whose thermal conductivities are different from each other, are used, alumina and gold were used. Such a combination is not limited thereto. In addition, for example, a combination of materials which are greatly different in thermal conductivities, is desirable, in case where a mental stress level is high.

Genes, which activate a homeostatic function, can be expressed by applying thermal stimuli to thermal-stimulus origin parts which are specific local parts of a body surface, using an electric type warm temperature heating stimulus apparatus.

In Table 7, subjects were adult men and women, and warm temperature heating stimuli were applied to stimulus parts using the above-mentioned electric type warm temperature heating stimulus apparatus. The Table 7 shows results in case where warm temperature heating stimuli were applied to thermal-stimulus origin parts, and the volume of blood flow was measured before and after the application of stimulus to a central part of a horizontal line of a wrist joint using a laser Doppler tissue rheometer. From the table, an increase in blood flow volume was recognized before and after the application of thermal stimuli. From the table, when the increase rate of blood flow is 60% or greater, preferably 120% or greater, the curative effect was remarkable.

What is claimed is:

1. A method for expressing a homeostatic function activating gene, comprising:
   applying a thermal stimulus, which is controlled to be a temperature of 40 degree Celsius to 50±5 degree Celsius, to a specific site on a body surface by utilizing an electric type warm temperature heating stimulus apparatus, thereby increasing a blood volume in a peripheral blood vessel or a cerebral blood vessel by 60% or more so as to express a gene which switches a homeostatic function on expression, thereby activating the gene,
   wherein the specific site is a part that intersects the perpendicular line of the medial malleolus on an extension line of the medial margin on os metatarsale primam 1 and 2 in a left and/or right foot sole, and
   the blood volume is measured based on a rate of a blood flow by a laser Doppler tissue blood flow meter which is attached to an inner and central part of a wrist joint.

2. The method for expressing the homeostatic function activating gene according to claim 1, wherein the thermal stimulus has a thermal stimulus pattern, the thermal stimulus pattern comprising independent thermal stimulus waveforms whose phases are shifted such that the thermal stimulus patterns do not substantially overlap each other.

* * * * *